United States Patent [19]
O'Lenick, Jr.

[11] Patent Number: 5,260,401
[45] Date of Patent: Nov. 9, 1993

[54] TERMINAL FLUORINE CONTAINING SILICONE POLYESTER COMPOUNDS

[75] Inventor: Anthony J. O'Lenick, Jr., Lilburn, Ga.

[73] Assignee: Siltech Inc., Norcross, Ga.

[21] Appl. No.: 57,171

[22] Filed: May 3, 1993

Related U.S. Application Data

[63] Continuation-in-part of Ser. No. 935,420, Aug. 26, 1992, Pat. No. 5,235,017, which is a continuation-in-part of Ser. No. 837,152, Feb. 19, 1992, Pat. No. 5,164,471.

[51] Int. Cl.$^5$ .................... C08G 77/24; C08G 77/445
[52] U.S. Cl. ......................... 528/26; 528/42; 528/25; 528/29; 525/474; 525/446
[58] Field of Search ............ 528/26, 42, 25, 29; 525/474, 446

[56] References Cited

U.S. PATENT DOCUMENTS

| | | | |
|---|---|---|---|
| 3,038,000 | 6/1962 | Schmidt | 528/42 |
| 3,511,699 | 5/1970 | Sterman | 117/35.5 |
| 4,812,518 | 3/1989 | Haubennestel et al. | 525/100 |
| 4,937,277 | 6/1990 | O'Lenick, Jr. | 524/318 |
| 5,051,489 | 9/1991 | O'Lenick, Jr. | 528/26 |
| 5,164,471 | 10/1992 | O'Lenick, Jr. | 528/26 |
| 5,210,133 | 5/1993 | O'Lenick, Jr. | 525/54.1 |

Primary Examiner—John C. Bleutge
Assistant Examiner—Margaret W. Glass

[57] ABSTRACT

The invention discloses novel fluorine containing polyester compounds. Compounds of the invention by virtue of (a) the silicone containing polyester group, (b) the fluorine containing terminal groups and (c) the polyoxyalkylene containing dimethicone copolyol group are extremely efficient lubricating materials when applied to a variety of surfaces and are water dispersible or water soluble depending upon the specific molecule. These materials have a water soluble portion in the silicone backbone which allows for the preparation of water dispersible and water soluble fluorine containing compounds useful in personal care applications as conditioners and softeners. The compounds of the present invention are prepared from terminal silicone containing dimethicone copolyols. This results in substantially linear polymers which form non-occlusive, hydrophobic films which are useful in barrier creams, automotive waxes and other lubricating compositions. These materials are prepared by reacting a terminal substituted dimethicone copolyol compound with a dicarboxylic acid and a fluorine containing alcohol.

15 Claims, No Drawings

TERMINAL FLUORINE CONTAINING SILICONE POLYESTER COMPOUNDS

RELATED APPLICATION

This application is a continuation in part of co-pending Ser. No. 935,420 filed Aug. 26, 1992 now U.S. Pat. No. 5,233,017 which is a continuation in part of U.S. application Ser. No. 837,152 filed Feb. 18, 1992 now U.S. Pat No. 5,164,471.

BACKGROUND OF THE INVENTION

1. Field of the Invention

The present invention relates to a series of novel fluorine containing silicone polyesters which provide films which are resistant to chemical agents, hydrophobic, non-occlusive, non comedogenic and highly lubricious when applied to fiber, metal, hair and skin. Unlike the compounds of the invention disclosed in the application of which this is a continuation in part, the compounds of the present invention are substantially linear and water dispersible or soluble. allowing for them to provide conditioning and breathable films when applied from aqueous solution to hair and skin. The esterification by which the compounds are prepared is the reaction of a terminal substituted dimethicone copolyol, a hydroxy containing silicone polymer which may contain varying amounts of polyoxyalkylene in the molecule, a dicarboxylic acid and a fluorine containing alcohol. Since the fluorine containing alcohol contains only one hydroxyl group, it will become a terminal group in the polyester.

2. Arts and Practices

Silicone compounds have been known to be active at the surface of plastic, cellulosic and synthetic fibers as well as paper. They are good nondurable lubricants and are very stable to oxidation, however, their high cost and lack of efficiency at low concentrations as well as low durability have made their acceptance in commercial products quite low. In all instances, commercially available quaternaries are the active ingredient in traditional laundry care markets, with little or no silicone added.

The low efficiency and low durability of dimethylpolysiloxane is due to the fact that it is very water insoluble and deposits on the surface to obtain a minimum free energy in the solution. Simply, the silicone oil delivery to the surface by hydrophobic binding, not chemical bonding. At the surface, the dimethylpolysiloxane is a very effective fiber lubricant, however, there are two drawbacks, first; the dimethylpolysiloxane is not chemically bonded so the effect is very transient and disappears with one washing, and second; since there is no reaction of the dimethylpolysiloxane to the surface an equilibrium between fiber absorbed dimethylpolysiloxane and dimethylpolysiloxane in the dispersion results in very inefficient percentage of silicone deposited. A large amount of the expensive silicone goes down the drain with the waste water.

In many applications, there is a strong desire to obtain a solid wax which can be used in applications were a spread on application is of interest. These applications include personal care applications like antiperspirants and skin creams. Unfortunately most silicone derivatives are liquid to very low temperatures. Attempts ot overcome this deficiency have been made by reacting stearyl alcohol with a chloro silane. The difficulty with the use of this type of material is that a large excess (50% by weight) of the alcohol needs to be added to get a product which is free of the irritating chlorosilane raw material. When such an excess is used the product behaves functionally more like the stearyl alcohol than like a silicone compound. Additionally, the compound is not polymeric, hence the superior lubrication and hydrophobicity enhancements which can be achieved by dimethylpolysiloxane is not obtainable with these compounds.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is a ether linkage and a new hydroxyl group. While a definite improvement over other compounds the efficiency and durability of the were not good enough to allow for cost effective incorporation of these materials in detergent formulations.

U.S. Pat. No. 5,051,489 issued to O'Lenick, Jr. teaches that silicone esters can be prepared by the reaction of silanols and fatty acids. These compounds lack the critical fluorine containing component.

THE INVENTION

Object of the Invention

It is the object of the present invention to provide a water dispersible substantially linear, fluorine containing dimethicone copolyol based polyester compound which is spreads our into a very thin durable film and provides outstanding conditioning when applied to a variety of surfaces, most importantly fiber, skin, hair and metal.

It is another objective of the current invention to provide fluorine containing polyesters which can be used in textile, and personal care applications to render softness and lubrication to the substrates being treated.

The incorporation of fluorine into the polyester results in the improved spreading and the ability to use these materials at heretofore unknown concentrations and still obtain efficacy. The use of terminal dimethicone copolyols as raw material hydroxy containing silicone compounds allows for the preparation of water dispersible to water soluble polyesters which are substantive to hair and skin. It is not possible to make water dispersible or water soluble materials using the technology disclosed in the related patent application, which are based upon silanol compounds. This is because there is no practical method of introducing the desired polyoxyalkylene moiety into the compound.

Summary of the Invention

The present invention relates to novel fluorine containing water dispersible or water soluble silicone polyester compounds. Compounds of the invention by virtue of (a) the polyester group, (b) the fluorine containing terminal groups and (c) the polyoxyalkylene portion of the molecule present in the dimethicone copolyol are extremely efficient lubricating materials when applied to a variety of surfaces and are water dispersible or water soluble. These materials spread out when applied and provide durable lubrication and hydrophobicity when applied to hair, skin, wood, plastic and textile fibers. The compounds of the present invention are prepared by reacting a dimethicone copolyol compound with a polycarboxylic acid and a fluorine containing alcohol.

The compounds of this invention are fluorine containing substantially linear dimethicone copolyol polyesters made by the esterification of a dicarboxylic acid, ester or anhydride, a terminal dimethicone copolyol compound and a fluorine containing alcohol. Specifically, the compounds of the present invention are fluorine containing polyester compounds which is prepared by the esterification reaction of;

(a) a dimethicone copolyol compound conforming to the following structure;

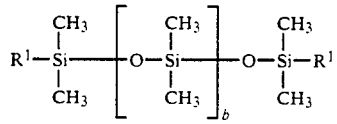

wherein;
$R^1$ is $-(CH_2)_3-O-(CH_2-CH_2-O)_x-(CH_2-CH(CH_3)-CH_2-O)_y-(CH_2-CH_2-O)_z-H$;

x, y and z are independently integers each ranging from 0 to 20;

(b) a diacid selected from the group consisting of $HO(O)C-(CH_2)_c-C(O)OH, HO(O)C-(CH_2)_d-CH=CH-(CH_2)_e-C(O)OH$ and dimer acid; c, d and e are independently integers from 1 to 10; and (c) a fluorine containing hydroxy compound conforming to the following structure;

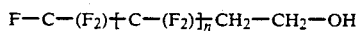

n is ranges from 3 to 17.

Dimer acid is well known to those skilled in the art and are prepared by the thermal condensation of unsaturated fatty acids catalyzed by a small amount of montmorillonite clay are described in numerous patents by C. G. Gobel (U.S. Pat. Nos. 2,482,761, 2,793,219, 2,793,220, 2,955,121, 3,076,003 and 3,100,784), incorporated herein by reference. Basically, dimer acid is the Diels Alder reaction of unsaturated mono fatty acids containing 18 carbon atoms, to produce a 36 carbon diacid. There are basically three structures which result. They are;

| UNSATURATED SPECIES | |
|---|---|
| STRUCTURE | DESIGNATION |
| $CH_3-(CH_2)_8-CH-(CH_2)_7-C(O)-OH$<br>$\hspace{2cm}\vert$<br>$CH_3-(CH_2)_7-CH=C-(CH_2)_7-C(O)-OH$ | Acyclic |
| 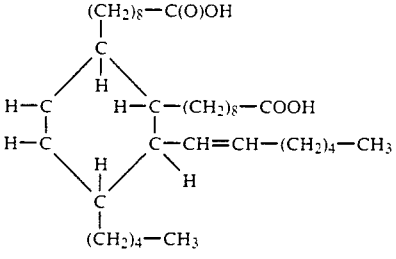 | Monocyclic |
| 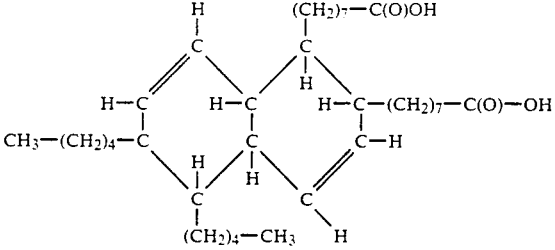 | Bicyclic | b is an integer ranging from 0 to 200;

The compounds are then hydrogenated to remove the double bonds to give the following;

| HYDROGENATED SPECIES | |
|---|---|
| STRUCTURE | DESIGNATION |
| $CH_3-(CH_2)_8-CH-(CH_2)_7-C(O)-OH$<br>$\hspace{2cm}\vert$<br>$CH_3-(CH_2)_7-CH_2CH-(CH_2)_7-C(O)-OH$ | Acyclic |

-continued
HYDROGENATED SPECIES

| STRUCTURE | DESIGNATION |
|---|---|
| (structure shown) | Monocyclic |
| (structure shown) | Bicyclic |

The above structures both in the hydrogenated and unsaturated forms are collectively referred to as "dimer acid" and the derivatives are referred to as those derived from a dimer acid residue.

PREFERRED EMBODIMENTS

In a preferred embodiment the fluorine content in the polymer ranges from 5% to 30% by weight.

In another preferred embodiment the fluorine content in the polymer ranges from 10% to 25% by weight.

In a preferred embodiment the diacid is dimer acid. This results in a material with superior conditioning effects on hair and skin and better compatibility in many organic oils.

In another preferred embodiment the diacid is dodecanedioic acid.

In a still another embodiment, the terminal dimethicone copolyol has present polyoxyalkylene glycol units. That is the sum of $x+y+z$ is greater than 0.

In a more preferred embodiment, the terminal dimethicone copolyol has present several polyoxyalkylene glycol units. That is the sum of $x+y+z$ is greater than 2.

In a more preferred embodiment, the terminal dimethicone copolyol has present several polyoxyalkylene glycol units. That is the sum of $x+y+z$ is greater than 5.

EXAMPLES

The compounds of the present invention are prepared by the reaction of a terminal dimethicone copolyol compound a diacid and a fluorine containing alcohol. Examples of suitable reactants are as follows;

| Reactants Diacids | Formula | Molecular Weight |
|---|---|---|
| Adipic Acid | HO(O)C(CH$_2$)$_4$C(O)OH | 130 |
| Succinic Acid | HO(O)C(CH$_2$)$_2$C(O)OH | 102 |
| Dodecanedioic Acid | HO(O)C(CH$_2$)$_{10}$C(O)OH | 230 |
| Dimer Acid | See Above | 286 |
| Maleic Acid | HO(O)C—CH=CH—C(O)OH | 100 |

Terminal Substituted Dimethicone Copolyol Compounds

Terminal substituted dimethicone copolyol compounds are well known and are marketed in the trade under many names.

The preferred method of placing this type of reactive hydroxyl group into the silicone polymer is by the reaction of terminal silanic hydrogen containing polymer with allyl alcohol alkoxylates. This technology is well known to those skilled in the art and are described in U.S. Pat. No. 4,083,856. These hydroxyl functional silicone compounds are subsequently esterified, by reaction with fatty acids, esters or anhydrides, to make the compounds of the present invention.

Compounds suitable for use as reactants in the preparation of the compounds ot the present invention conform to the following structure:

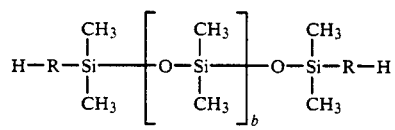

R is —(CH$_2$)$_3$—O—(CH$_2$CH$_2$—O)$_x$—(CH$_2$(CH$_3$)-CH—O)$_y$—(CH$_2$CH$_2$—O)$_z$— x, y and z are integers independently ranging from 0 to 20;

b is an integer from 1 to 200.

These materials are available from Siltech Inc. Norcross, Ga. and are marketed under the Siltech T series tradename.

| Name | x | y | z | Molecular Weight |
|---|---|---|---|---|
| Siltech T 701 | 0 | 0 | 0 | 1,000 |
| Siltech T 706 | 5 | 1 | 0 | 6,000 |
| Siltech T 710 | 2 | 1 | 1 | 10,000 |
| Siltech T 750 | 10 | 5 | 10 | 50,000 |
| Siltech T 790 | 20 | 20 | 20 | 86,000 |

Fluorine Containing Alcohols

Fluorine containing alcohols are commercially available from a variety of suppliers, most importantly DuPonte Performance Products Division. They conform to the following structure;

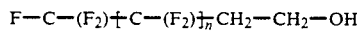

$$F-C-(F_2)+C-(F_2)_n^-CH_2-CH_2-OH$$

n is ranges from 3 to 17.

| Reactant Example Number | n Value | Molecular Weight | % F |
|---|---|---|---|
| 1 | 3 | 264 | 64.7 |
| 2 | 5 | 364 | 67.8 |
| 3 | 7 | 464 | 69.6 |
| 4 | 9 | 564 | 70.7 |
| 5 | 11 | 664 | 71.5 |
| 6 | 13 | 764 | 72.1 |
| 7 | 15 | 864 | 72.5 |
| 8 | 17 | 964 | 72.9 |

Compounds of the Invention

The reaction can be run with varying amounts of fluorine containing alcohol. It should be clear that since only the fluorine containing material contains only one hydroxyl group it will be chain terminating. The other materials, namely the dimethicone copolyol and the diacid each have two functional groups.

Polymers of the following structure will result;

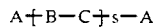

$$A+B-C+s-A$$

wherein:
A is the fluorine containing portion
B is the diacid
C is the dimethicone copolyol The less amount of "A" used, the higher the "s" value, and the lower the fluorine content. That is because "A" is both a chain stopper and the fluorine source.

| | "A" Concentration High | "A" Concentration Low |
|---|---|---|
| Concentration | High | Low |
| Molecular weight | Low | High |
| Fluorine Content | High | Low |
| "s" value | Low | High |

General Reaction Conditions

The esterification can be run without catalyst; however, when no catalysts used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc. The most preferred catalyst is stannous oxylate. The reaction is conducted at between 140° and 240° C. under an inert nitrogen blanket. The nitrogen blanket preserves the color. Preferred temperature range is between 180° and 210° C. Water is removed from the reaction which is done using a nitrogen sparge or vacuum.

EXAMPLES

General Procedure

Into a suitable round bottom, three neck flask equipped with a Dean Stark trap, a thermometer and a nitrogen sparge is added the specified number of grams of the diacid, the specified number of grams of dimethicone copolyol, the specified number of grams of fluorine containing alcohol and 0.25% of total weight of the batch of catalyst. The reaction mass is blanketed with nitrogen, and heated to 180° and 200° C. under an inert nitrogen blanket. Once the reaction temperature reaches 120° C. water begins to boil off and is collected in the Dean Stark Trap. Within four to five hours the theoretical water is collected off and the acid value is very low. The product is used without additional purification.

EXAMPLE 9

Into a suitable round bottom, three neck flask equipped with a Dean Stark trap, a thermometer and a nitrogen sparge is added the specified number of 130.0 grams of the Adipic Acid (the diacid), the 5,000.0 grams of Siltech T-701 (the dimethicone copolyol), 264. 0 grams of Reactant Example 1, (the fluorine containing alcohol) and 0.25% of total weight of the batch of catalyst. The reaction mass is blanketed with nitrogen, and heated to 180° and 200° C. under an inert nitrogen blanket. Once the reaction temperature reaches 120° C. water begins to boil off and is collected in the Dean Stark Trap. Within four to five hours the theoretical water is collected off and the acid value is very low. The product is used without additional purification.

EXAMPLE 10-33

Example 9 is repeated only this time substituting the specified number of grams of the specified diacid for the dimer acid and the specified type and number of grams of dimethicone copolyol and the specified type and number of grams of fluorine containing compound as shown below;

Note; In the below table Gms. is grams.

| Example | Diacid | "F" Alcohol | Terminal Dimethicone Copolyol |
|---|---|---|---|
| 10 | Succinic Acid 102.0 Gms. | Reactant Example 2 364.0 Gms. | T-701 500 gms |
| 11 | Dodecanedioic Acid 230.0 Gms. | Reactant Example 3 464.0 Gms. | T-706 3,000 gms |
| 12 | Dimer Acid 286.0 Gms. | Reactant Example 4 564.0 Gms. | T-710 5,000 gms |
| 13 | Hydrogenated Dimer Acid 286.0 Gms. | Reactant Example 5 664.0 Gms. | T-750 25,000 gms |
| 14 | Maleic Acid 100.0 Gms. | Reactant Example 6 764.0 Gms. | T-790 45,000 gms |
| 15 | Adipic Acid 130.0 Gms. | Reactant Example 7 864.0 Gms. | T-701 500 gms |

-continued

| Example | Diacid | "F" Alcohol | Terminal Dimethicone Copolyol |
|---|---|---|---|
| 16 | Succinic Acid 102.0 Gms. | Reactant Example 8 964.0 Gms. | T-706 6000 gms |
| 17 | Dodecanedioic Acid 230.0 Gms. | Reactant Example 1 264.0 Gms. | T-710 5000 gms |
| 18 | Dimer Acid 286.0 Gms. | Reactant Example 2 364.0 Gms. | T-701 1000 gms |
| 19 | Hydrogenated Dimer Acid 286.0 Gms. | Reactant Example 3 464.0 Gms | T-706 3000 gms |
| 20 | Maleic Acid 100.0 Gms. | Reactant Example 4 564.0 Gms. | T-701 1000 gms |
| 21 | Adipic Acid 130.0 Gms. | Reactant Example 5 664.0 Gms. | T-701 500 gms |
| 22 | Succinic Acid 102.0 Gms. | Reactant Example 6 764.0 Gms. | T-701 500 gms |
| 23 | Dodecanedioic Acid 230.0 Gms. | Reactant Example 7 432.0 Gms. | T-701 1000 gms |
| 24 | Dimer Acid 286.0 Gms. | Reactant Example 8 964.0 Gms | T-706 3000 gms |
| 26 | Hydrogenated Dimer Acid 286.0 Gms. | Reactant Example 1 133.0 Gms. | T-750 50000 gms |
| 27 | Maleic Acid 100.0 Gms. | Reactant Example 2 50.0 Gms. | T-750 25000 gms |
| 28 | Adipic Acid 130.0 Gms. | Reactant Example 3 464.0 Gms. | T-710 5000 gms |
| 29 | Succinic Acid 102.0 Gms. | Reactant Example 4 564.0 Gms. | T-750 50000 gms |
| 30 | Dodecanedioic Acid 230.0 Gms. | Reactant Example 5 664.0 Gms. | T-750 25000 gms |
| 31 | Dimer Acid 286.0 Gms. | Reactant Example 6 764.0 Gms. | T-790 90000 gms |

APPLICATIONS EXAMPLES

The compounds of the present invention can be used in a variety of applications were a thin film of is desired. They can be utilized to formulate outstanding barrier creams. The products form films which are hydrophobic, nonocclusive and non comedogenic.

Some examples are:

Rouge

A typical formulation is:

| Material | % |
|---|---|
| Stearyl Alcohol | 7.0 |
| Example 24 | 5.0 |
| Exxal 20 | 5.0 |
| Ethanol | 5.0 |
| Magnesium Stearate | 2.0 |
| Kaolin | 15.0 |
| Starch | 5.0 |
| Magnesium carbonate | 2.0 |
| Talc | 44.0 |
| Titanium dioxide | 5.0 |
| Powder brown (color) | 5.0 |

Eyeshadow

The compounds of the invention can be utilized to formulate eyeshadow products. A typical formulation is;

| Material | % |
|---|---|
| Stearyl Alcohol | 55.0 |
| Example 31 | 20.0 |
| Ozokerit 70-72 | 15.0 |
| Color (Ariabel 300 403 | 10.0 |

Lip Stick Formulation

The compounds of this invention make outstanding bases for the preparation of lipstick products. The lipsticks made with these materials have outstanding slip and provide lubrication and emmoliency properties to the stick. A typical formulation is;

| Material | % |
|---|---|
| Stearyl alcohol | 40.0 |
| Example 24 | 40.0 |
| Exxal 20 | 10.0 |
| Color | 5.0 |
| Titanium dioxide | 5.0 |

Lipcream

By replacing the C-20 guerbet alcohol with a guerbet citrate ester and altering the ratio of components a lipcream can be formulated;

| Material | % |
|---|---|
| Stearyl alcohol | 40.0 |
| Example 24 | 40.0 |
| Siltech CE-2000 | 15.0 |
| Color | 3.0 |
| Titanium dioxide | 2.0 |

What is claimed:

1. A fluorine containing silicone polyester compound which is prepared by the esterification reaction of;
   (a) a terminal dimethicone copolyol compound conforming to the following structure;

$$R^1-\underset{\underset{CH_3}{|}}{\overset{\overset{CH_3}{|}}{Si}}-\left[O-\underset{\underset{CH_3}{|}}{\overset{\overset{CH_3}{|}}{Si}}\right]_b-O-\underset{\underset{CH_3}{|}}{\overset{\overset{CH_3}{|}}{Si}}-R^1$$

wherein;

$R^1$ is $-(CH_2)_3-O-(CH_2-CH_2-O)_x-(CH_2-CH(CH_3)-CH_2-O)_y-(CH_2-CH_2-O)_z-H$;

b is an integer ranging from 0 to 200;

x, y and z are independently integers each ranging from 0 to 20;

(b) a diacid selected from the group consisting of $HO(O)C-(CH_2)_c-C(O)OH, HO(O)C-(CH_2)_d-CH=CH-(CH_2)_e-C(O)OH$ and dimer acid;

c, d and e are independently integers from 1 to 10; and (c) a fluorine containing hydroxy compound conforming to the following structure;

$$F-C-(F_2)+C-(F_2)\frac{1}{n}CH_2-CH_2-OH$$

n is ranges from 3 to 17.

2. A compound of claim 1 wherein the fluorine content in the compound ranges from 5% to 30% by weight.

3. A compound of claim 1 wherein the fluorine content in the compound ranges from 10% to 25% by weight.

4. A compound of claim 1 wherein the diacid is dimer acid.

5. A compound of claim 1 wherein the diacid is dodecanedioic acid.

6. A compound of claim 1 wherein $x+y+z$ is greater than zero.

7. A compound of claim 1 wherein n ranges from 3 to 11.

8. A compound of claim 1 wherein n is 3.

9. A compound of claim 1 wherein n is 5.

10. A compound of claim 1 wherein n is 7.

11. A compound of claim 1 wherein n is 9.

12. A compound of claim 1 wherein n is 11.

13. A compound of claim 1 wherein n is 13.

14. A compound of claim 1 wherein n is 15.

15. A compound of claim 1 wherein n is 17.

* * * * *